US008303998B2

(12) United States Patent
Wehrli et al.

(10) Patent No.: US 8,303,998 B2
(45) Date of Patent: Nov. 6, 2012

(54) PROCESS FOR EXTRACTION OF GLUCOSINOLATES FROM BROCCOLI SEEDS

(75) Inventors: Christof Wehrli, Witterswil (CH); Jan Schütz, Lörrach (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/058,458

(22) PCT Filed: Aug. 21, 2009

(86) PCT No.: PCT/EP2009/060824
§ 371 (c)(1),
(2), (4) Date: Feb. 10, 2011

(87) PCT Pub. No.: WO2010/023162
PCT Pub. Date: Mar. 4, 2010

(65) Prior Publication Data
US 2011/0135766 A1   Jun. 9, 2011

(30) Foreign Application Priority Data

Aug. 27, 2008  (EP) ..................................... 08163089
Dec. 16, 2008  (EP) ..................................... 08171823

(51) Int. Cl.
*A01N 65/00* (2009.01)
(52) U.S. Cl. ...................................................... 424/725
(58) Field of Classification Search ........................ None
See application file for complete search history.

(56) References Cited

FOREIGN PATENT DOCUMENTS
WO   2004/089065   10/2004

OTHER PUBLICATIONS

International Search Report for PCT/EP2009/060824, mailed Dec. 9, 2009.
Written Opinion for PCT/EP2009/060824, mailed Dec. 9, 2009.
Troyer et al., Analysis of Glucosinolates from Broccoli and other Cruciferous Vegetable by Hydrophilic Interaction Liquid Chromatoraphy, Journal of Chromatography, Elsevier Sceince Publishers B.V. Amsterdam, NL, vol. 919, No. 2, Jun. 15, 2001, pp. 299-304, XP004248013.
Moreno et al., "Chemical and Biological Characterisation of Nutraceutical Compounds of Broccoli", Journal of Pharmaceutical and Biomedical Analysis, New York, NY, US, vol. 41, No. 5, Aug. 28, 2000, pp. 1508-1522, XP025145874.
Elfakir et al., Comparison of a Styrene-Divinylbenzene Copolmeric Anion Exchanger and a Polymethacrylate Copolymeric Anion Exchanger for Glucosinolate Separation, Journal of Liquid Chromatography and Related Technologies 1997 US, vol. 20, No. 6, 1997 US, vol. 20, No. 6, 1997, pp. 907-921, XP008114041.
Prestera et al., "Comprehensive Chromatographic and Spectroscopic Methods for the Separation and Identification of Intact Glucosinolates", Analytical Biochemistry 1996, US, vol. 239, No. 2, Aug. 1, 1996, pp. 168-179, XP002552044.
Trenerry et al., "The Determination of Glucoraphanin in Broccoli Seeds and Florets by Solid Phase Extraction and Micellar Electrokinetic Capillary Chromatography", Food Chemistry, Elsevier Science Publishers LTD., GB, vol. 98, No. 1, Jan. 1, 2006, pp. 179-187, XP025129879.
Chen et al., "In vivo Synthesis and Purification of Radioactive P-Hydroxybenzylglucosinolate in Sinapis Alba L.", Phytochemical Analysis 200005 GB, vol. 11, No. 3, May 2000, pp. 174-178, XP002552043.
West et al., "Single Column Approach for the Liquid Chromatographic Separation of Polar and non-polar Glucosinolates from Broccoli Sprouts and Seeds", Journal of Chromatography, Elsevier Science Publishers B.V. Amsterdam, NL, vol. 966, No. 1-2, Aug. 9, 2002, pp. 227-232, XP004372036.
Toribio et al., "Strong Ion-Exchange Centrifugal Partition Chromatography as an Efficient Method for the Large-Scale Purification of Glucosinolates", Journal of Chromatography, Elsevier Science Publishers B.V. Amsterdam, NL, vol. 1170, No. 1-2, Oct. 11, 2007, pp. 44-51, XP022296349.
Fisher et al., "Technology Transfer and Scale up of a Potential Cancer-Preventive Plant Dynamic Extraction of Glucoraphanin", Journal of Liquid Chromatography and Related Technologies, Monticello, NY, US, vol. 28, Jul. 1, 2005, pp. 1913-1922, XP008081407.
Rochfort et al., "The Isolation and Purification of Glucoraphanin from Broccoli Seeds by Solid Phase Extraction and Preparative High Performance Liquid Chromatography", Journal of Chromatography, Elsevier Science Publishers B.V. Amsterdam, NL, vol. 1120, No. 1-2, Jul. 7, 2006, pp. 205-210, XP024987225.

*Primary Examiner* — Michael Meller
(74) *Attorney, Agent, or Firm* — Nixon & Vanderhye P.C.

(57) ABSTRACT

A new process for extracting and purifying glucosinolates from plant material, preferably broccoli sprouts or seeds is described. An alcoholic extract is adsorbed onto a basic resin and eluted with ammonia. Optionally, the alcoholic extract is passed through an ion-exchange column containing acidic resin prior to the adsorption/elution step.

10 Claims, No Drawings

PROCESS FOR EXTRACTION OF GLUCOSINOLATES FROM BROCCOLI SEEDS

This application is the U.S. national phase of International Application No. PCT/EP20091060824, filed 21 Aug. 2009, which designated the U.S. and claims priority to European Application No. 08163089.9, filed 27 Aug. 2008 and European Application No. 08171823.1, filed 16 Dec. 2008, the entire contents of each of which are hereby incorporated by reference.

BRIEF DESCRIPTION OF THE INVENTION

This invention relates to a process for extracting glucosinolates from broccoli seeds, sprouts, or florets which comprises a step of adsorbing a broccoli seed extract on a basic resin, followed by elution of the adsorbed glucosinolates and collecting the glucosinolate-rich eluate.

BACKGROUND OF THE INVENTION

Broccoli seeds have a high amount of glucosinolates, including glucoraphanin, glucoiberin, glucoerucin. While the glucosinolates are not biologically active, cleavage by the enzyme myrosinase (present in many plant cells and in the gut microflora) results in the formation of active isothiocyanates. These isothiocyanates, including sulforaphane, have been shown to have numerous health-promoting properties, and in some experiments have even been shown to exert various anti-cancer effects.

Previously, various authors have developed extraction/purification schemes to obtain glucoraphanin from broccoli seeds. For example, West et al. 2002 *J. Chromatog A* 966: 227-232 describes use of ion-pair and hydrophilic interaction chromatographies for purifying various glucosinolates. See also Toribio et al. 2007 *J. Chromatog A* 1170:44-51 which describes purification of sinalbin and glucoraphanin using strong ion-exchange displacement centrifugal partition chromatography. However, both these techniques are directed to purification of compounds, and not merely extracting a glucoraphanin-containing extract from broccoli seeds which is economical and uses food-grade reagents.

It would be desirable to have a simple, robust glucosinolate extraction method which is suitable for production of food-grade or nutraceutical-grade glucosinolates, especially glucoraphanin.

DETAILED DESCRIPTION ON THE INVENTION

A new process for the production of a glucosinolate-containing extract has been developed in accordance with this invention, which comprises the steps of
 a) extracting glucosinolate-containing plant parts or seeds, or an extract of glucosinolate-containing plant parts or seeds with an extraction medium that comprises a lower alcohol or ketone or an aqueous mixture of a lower alcohol or ketone to obtain a alcoholic or ketonic extract;
 b) optionally completely or partially evaporating the extraction medium of step a);
 c) optionally contacting the extract of step a) or step b) with a cation exchange resin;
 d) adsorbing the extract from step a), step b), or step c) onto a basic resin; and
 e) optionally eluting the resulting glucosinolate-containing extract.

Suitable solvents for step b) through e) include water, C1-4 alcohols, C3-4 ketones, and mixtures thereof.

The cation exchange resin is preferably in its acidic form, and more preferably a strong acidic ion exchanger is used.

If desired, an additional step may be performed on the glucosinolate-containing extract obtained from step e). In this embodiment of the invention, the volatiles of the glucosinolate-containing extract are evaporated. The result of this step is a solid extract containing glucosinolates, which includes glucoraphanin, glucerucin, and glucoiberin. The solid extract made by this process also forms another aspect of this invention.

The starting materials for this invention may be any glucosinolate-containing plant material, or any glucosinolate-containing extract. Preferably, the plant material is from the Brassicaceae family, such as broccoli, mustard, rapeseed, cauliflower, kohlrabi, cabbage, bok choy, turnip, radish, wasabi, horse radish and brussel sprouts.

The plant parts may be the sprouts or seeds, as it is known that sprouts and seeds often contain higher amounts of glucosinolates than mature plant leaves, but florets or heads may also be used. If desired, the plant parts may be first subjected to a pre-treatment step of washing, or de-fatting (for seeds). In preferred embodiments, the plant is a broccoli plant, and seeds are extracted. In this case, the original starting material for the process may be either a broccoli seed extract or the broccoli seeds themselves.

If one starts with plant parts, optionally washed and/or defatted and/or otherwise treated, then they are subjected to an extraction step. In this extraction, it is preferable to use an aqueous medium, or a lower alcohol or ketone wherein a lower alcohol or ketone is a C1 to C4 alcohol or ketone or mixtures thereof. This may be performed in the presence of charcoal or other similar material such as celite. See, for example Toribio et al., supra. The extract obtained can then be used in the next step. If desired, the extract can be subjected to further purification steps such as ultrafiltration. Also the extract may be optionally concentrated by a complete or partial evaporation of the solvent.

In the next step, the extract of plant parts (either as obtained above, or, optionally, a commercially available extract) is then extracted with an extraction medium which comprises a lower alcohol or lower ketone. The term "lower alcohol" or "lower ketone" means that the alcohol is a C1-C4 alcohol or the ketone is a C3-C4 ketone, or mixtures thereof; and is preferably an alcohol or ketone which is approved for use in food manufacturing, such as ethanol or acetone, although using technical ethanol may also be used. The alcohol or ketone are preferably ethanol or acetone, and may be in an aqueous solution such as at least about 40% alcohol or ketone; in a preferred embodiment, the lower alcohol or lower ketone is at least about 70% in an aqueous solution, and in a more preferred embodiment it is from about 70% to about 95%. In this step, temperature is not particularly critical. The extract may be filtered or decanted to separate the solubles from the insolubles.

The extract may be evaporated to remove the volatiles, followed by dissolving in an appropriate solvent such as water, lower alcohols, ketones, or a mixture thereof for the next step.

Optionally, the alcoholic or ketonic extract in the appropriate solvent or solvent mixture is subjected to a cationic ion-exchange column, preferably a strong acidic resin, in its acidic form such as DOWEX® 50W or AMBERLYST® 15 (both available from Sigma Aldrich). It is also preferred, in keeping with the intended use of the final product as a nutraceutical or food ingredient, that the resin is chosen as to meet regulatory requirements for food production.

The extract which is obtained from either the alcoholic extraction step, or preferably the ion-exchange step, is then adsorbed onto a basic resin. The basic resin may be either a strongly or weakly basic resin, preferably a weakly basic resin. Examples of suitable resins include AMBERLITE® IRA-67, and LEWATIT® VPOC 1065, (both available from Sigma Aldrich). In keeping with the goal of manufacturing nutraceutical/food grade material, it is preferred that the resin be suitable from a regulatory view for this purpose. For this step, temperature is not particularly critical; ambient temperature is preferred.

The ion-exchange column so-prepared is then eluted with a base such as ammonia, diluted potassium hydroxide, sodium hydroxide, sodium carbonate, sodium hydrogen carbonate or the like, in water, lower alcohol (C1-C4) or acetone or in mixtures thereof. The preferred base is ammonia in water, lower alcohol (C1-C4) or mixtures of the solvents.

The resulting eluate (final extract) contains glucosinolates in a more purified form than the original starting material. While actual amounts of major products may vary from lot-to-lot, depending on the content of the starting plant material; a typical final extract will contain the following major glucosinolates: glucoraphanin, glucoerucin, and glucoiberin. This product forms yet another embodiment of this invention.

If desired, the final extract may be evaporated, freeze-dried or spray-dried using conventional means so that it is a solid extract. These processed solid extracts also form an aspect of this invention.

In one preferred embodiment of the invention, the extract after ion exchange treatment and elution with ammonia, contains the ammonium salt of glucoraphanin as a major product. In an optional, but preferred step, the ammonium salt is changed into an ammonium-free extract suitable for further processing. In this optional step, the extract which is acidic, is made more basic. This can be done by adding any conventional source of base, such as alkali- or earth alkali hydroxides, such as magnesium hydroxide, calcium hydroxide, sodium hydroxide, potassium hydroxide. Preferably the base is suitable for use in food, such as sodium hydroxide.

Enough base is added so that the pH rises to above 7.0, more preferably to about pH 7 to pH 12, and even more preferably to pH 9 to 11.

The addition of a base such as sodium hydroxide to form a basic environment, such as from pH 9 to 11, allows the exchange of ammonium ions to sodium ions. The volatiles can then be separated from the resulting sodium glucosinolate by conventional means, such as by use of reduced pressure (i.e. removed using a partial vacuum), resulting an-ammonium free extract.

The following non-limiting Examples better illustrate the invention

Example 1

An extraction was made following the procedure generally described in A. Toribio et al.; *J. Chromatogr. A* 1170 (2007) 44-51, which is hereby incorporated by reference. 3 kg of broccoli seeds were stirred for 2 h in 20 liters of water at reflux temperature. The resulting warm solution was filtered. The filtrate was then agitated for 2 h with 150 g of charcoal. The suspension was filtered and concentrated at reduced pressure at 60° C. to 310 g residue with a glucoraphanin content of 12%.

Example 2

4.0 g of the residue of Example 1 was suspended in 40 ml of an ethanol:water (82%:18%) mixture and heated to reflux for approximately 30 min. The resulting suspension was filtered and the mother liquid was evaporated under reduced pressure (30 mbar) at 60° C. An extract was obtained (2.2 g) with a purity of glucoraphanin of 16%.

Example 3

2 g ion exchanger AMBERLITE® IRA-67 was stirred with 2.0 g extract of Example 1 in 10 ml water for 30 min. The liquid was removed by filtration and the loaded ion exchanger washed with water (5 ml). The loaded ion exchanger was stirred at ambient with 10 ml 5% aqueous ammonium hydroxide solution in methanol for 30 min. After filtration, the filtrate was evaporated under reduced pressure (30 mbar, 70° C.).

The result was 97.3 mg of extract containing glucoraphanin with a purity of 54%

Example 4

Washing the loaded ion exchanger of Example 3 with 10 ml 5% aqueous ammonium hydroxide solution in water yielded, after evaporation 217 mg glucoraphanin with a purity of 19%.

Example 5

2 g acidic ion exchanger AMBERLYST® 15 was stirred with 1 g extract of Example 2 in 10 ml water for 30 min at ambient temperature. The liquid was removed by filtration and the ion exchanger washed with water (5 ml). The eluate, containing the free glucoraphanin acid, was stirred with the weakly basic ion exchanger AMBERLYST® IRA-67 (2 g) for 30 min. at ambient temperature. The liquid was removed by filtration and the loaded ion exchanger washed with water (10 ml). The loaded ion exchanger was stirred with 10 ml of a solution of 5% aqueous ammonia in methanol for 30 min at ambient. After filtration, the eluate was evaporated under reduced pressure (30 mbar, 70° C.). Yield: 95.2 mg glucoraphanin with a purity of 69% (determined by HPLC).

Example 6

Washing the loaded basic ion exchanger from Example 5 with 5% aqueous ammonium hydroxide solution in water yielded after evaporation, 385.3 mg glucoraphanin (purity 25%).

Example 7

1 g of the extract of Example 5 was stirred in 10 ml water. An aqueous solution of sodium hydroxide (1 N) was added until a pH of 10.5 was reached. The mixture was stirred for 30 min at room temperature and the volatiles were removed under reduced pressure (30 mbar, 70° C.). Yield: 980 mg glucoraphanin with a purity of 64% (determined by HPLC). 42% of the ammonium ions were exchanged to sodium ions.

What is claimed is:
1. A process for obtaining a glucosinolate-rich eluate from broccoli seeds in an amount sufficient for production of food-grade or nutraceutical-grade glucosinolates, the process consisting essentially of:
   a) extracting a glucosinolate-containing extract from broccoli seeds with an extraction medium that comprises a lower alcohol or ketone or a mixture thereof with water, to obtain an alcoholic or ketonic glucosinolate-containing extract;

b) contacting the glucosinolate-containing extract of step a) with a cation ion-exchange resin of a cationic ion-exchange column;

c) adsorbing the glucosinolate-containing extract from step b) onto a basic resin of a basic ion-exchange column to obtain an adsorbed glucosinolate-containing extract; and d) eluting the adsorbed glucosinolate-containing extract of step c) by adding sufficient base to increase the pH to at least 7.0 to form glucosinolate-containing salts having alkali- or earth-alkali cations, and separating the resulting glucosinolate-containing salts to obtain the glucosinolate-rich eluate from broccoli seeds.

2. A process according to claim 1, wherein volatiles of the eluate are evaporated.

3. A process according to claim 1, wherein the cation exchange resin of step b) is a strongly acidic resin.

4. A process according to claim 1, wherein the alcohol of step a) is a C1-C4 alcohol.

5. A process according to claim 4 wherein the alcohol is ethanol.

6. A process according to claim 1, wherein the ketone of step a) is acetone.

7. A process according to claim 4, wherein the C1-C4 alcohol or acetone is present in an aqueous solution at a concentration of at least about 40%.

8. A process according to claim 5 wherein ethanol is present in the extraction medium at about 70% to about 95%.

9. The process of claim 1, wherein the eluate is evaporated, freeze-dried or spray-dried to obtain a solid glucosinolate-rich extract.

10. A process according to claim 1, wherein separation of the resulting glucosinolate-containing salts is performed by removing volatiles under reduced pressure.

* * * * *